United States Patent
Ginsberg

(10) Patent No.: US 7,404,796 B2
(45) Date of Patent: Jul. 29, 2008

(54) SYSTEM FOR DETERMINING INSULIN DOSE USING CARBOHYDRATE TO INSULIN RATIO AND INSULIN SENSITIVITY FACTOR

(75) Inventor: Barry H. Ginsberg, Wyckoff, NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 676 days.

(21) Appl. No.: 10/788,475

(22) Filed: Mar. 1, 2004

(65) Prior Publication Data

US 2005/0192494 A1   Sep. 1, 2005

(51) Int. Cl.
 *A61B 5/00* (2006.01)
 *A61B 5/05* (2006.01)
 *A61M 31/00* (2006.01)
(52) U.S. Cl. .................. 600/365; 600/300; 604/65; 604/66
(58) Field of Classification Search ............... 600/365; 604/66
See application file for complete search history.

(56) References Cited

U.S. PATENT DOCUMENTS

| | | | | |
|---|---|---|---|---|
| 4,832,603 | A | 5/1989 | Basil | 434/127 |
| 5,364,346 | A | 11/1994 | Schrezenmeir | 604/504 |
| 5,536,249 | A | 7/1996 | Castellano et al. | 604/65 |
| 5,582,598 | A | 12/1996 | Chanoch | 604/208 |
| 5,827,232 | A | 10/1998 | Chanoch et al. | 604/208 |
| 6,425,863 | B1 | 7/2002 | Werner et al. | 600/365 |
| 6,487,429 | B2 | 11/2002 | Hockersmith et al. | 600/316 |
| 6,551,276 | B1 | 4/2003 | Mann et al. | 604/131 |
| 6,554,798 | B1 | 4/2003 | Mann et al. | 604/131 |
| 6,558,351 | B1 | 5/2003 | Steil et al. | 604/131 |
| 6,641,533 | B2 | 11/2003 | Causey, III et al. | 600/300 |
| 2003/0028089 | A1* | 2/2003 | Galley et al. | 600/365 |
| 2003/0055570 | A1* | 3/2003 | Ribeiro, Jr. | 702/19 |
| 2003/0114836 | A1* | 6/2003 | Estes et al. | 604/890.1 |

OTHER PUBLICATIONS

"Carbohydrate Couting", Diabetes Program of PEI, Jul. 2002. pp. 1-7.
Bruce W. Bode, et al. "Insulin Pump Therapy in the 21 Century", Postgraduate Medicine Online, vol. 111, No. 5, May 2002. pp. 1-14, http://www.postgradmed.com/issues/2002/05_02/bode3.htm, printed on Dec. 5, 2002.

(Continued)

*Primary Examiner*—Robert L. Nasser, Jr.
*Assistant Examiner*—Patricia Mallari
(74) *Attorney, Agent, or Firm*—Roylance, Abrams, Berdo & Goodman, L.L.P.

(57) ABSTRACT

An apparatus and method are provided for determining a patient's carbohydrate to insulin ratio (CIR) and insulin sensitivity factor (ISF), and using these values, along with values for current blood glucose level and deviation from target blood glucose level, for determining insulin dose in view of carbohydrate intake during a particular time period. The apparatus and method employ algorithms that can be implemented in any of a personal computer, personal data assistant, hand held computing device, blood glucose monitor, infusion pump, medication delivery pen, meter, calculator, among other therapeutic, diagnostic or informational devices used for managing a patient's blood glucose levels.

34 Claims, 8 Drawing Sheets

OTHER PUBLICATIONS

"Insulin Pumper's Ratio Calculator", Version 1.04, last updated Mar. 29, 1991, pp. 1-2, http://insulin-pumpers.org/howto/ratio.cgi, printed on Dec. 5, 2003.

"1500 Rule", Therasense/Ask the Educator/ Questions and Answers, pp. 1-3, http://www.therasense.com/educator/questions/pattern_2.htm, printed on Dec. 5, 2003.

"Diabetes Calculations", pp. 1-2, http://world.std.com/-1word/dibetes/Calculate.html, printed on Dec. 5, 2003.

"Correction Factor From the 1800 Rule", pp. 1-2, http://www.diabetesenet.com/diabetes_control_tips/1800rule.php, printed on Dec. 5, 2003.

"Carb Counting", pp. 1-7, http://www.diabetesnet.com/diabetes_food_diet/carb_counting.php, printed on Dec. 3, 2003.

"Intensive Insulin Therapy", pp. 1-6, http://www.bddiabetes.com/us/yourinsulin/therapy_intensive.jsp, prtinted on Dec. 3, 2003.

* cited by examiner

SYSTEM FOR DETERMINING INSULIN DOSE USING CARBOHYDRATE TO INSULIN RATIO AND INSULIN SENSITIVITY FACTOR

CROSS-REFERENCE TO RELATED APPLICATIONS

Related subject matter is disclosed in a U.S. patent application of Gordon et al, entitled "A System and Method for Integrating Data with Guidelines to Generate Displays Containing the Guidelines and Data", Ser. No. 09/985,173, filed Nov. 1, 2001; and in a U.S. patent application of Gordon, entitled "System and Method for Assessment and Corrective Action Based on Guidelines", Ser. No. 10/153,883, filed May 24, 2002; the entire contents of both applications being incorporated herein by reference.

FIELD OF THE INVENTION

The invention relates generally to blood glucose meters and glucose monitoring for managing diabetes and, more particularly, to providing patients undergoing intensive insulin therapy with a convenient method for determining their insulin dosage based on their carbohydrate to insulin ratio (CIR) and insulin sensitivity factor (ISF, and sometimes called the correction factor) and for determining the values of the CIR and ISF directly from a series of patient data points.

BACKGROUND OF THE INVENTION

A significant number of people are undergoing intensive insulin therapy to manage their diabetes, whereby they determine their blood glucose level at each meal (e.g., breakfast, lunch, dinner, snack time) for use with other factors to assess the insulin dose needed. Intensive insulin therapy usually involves injections of regular-acting or rapid-acting insulin before each meal (i.e., bolus dose), as well as one or more injections of intermediate-acting or long-acting insulin every day (i.e., basal dose) or the use of an insulin pump to provide both the basal and bolus doses. By adjusting the amount of insulin to match blood sugar levels and the amount eaten at each meal, the goal of intensive insulin therapy is to keep blood sugar levels at or near normal throughout the day.

People on intensive insulin therapy use guidelines provided by their doctor to base the amount of insulin that they will need on what they are planning to eat, how much activity they plan to do, and what their current blood glucose level is. With this kind of planning, they have a lot of flexibility in what they can eat, when they can eat, and how active they can be. As discussed in more detail below, intensive insulin therapy requires diabetes education, careful planning, and strong commitment to be safe and successful. Patients must learn how food, exercise, and insulin affect their blood sugar, and adjust their insulin to keep their blood sugar levels within a target range.

The amount of carbohydrates in a patient's diet directly affects the amount and type of insulin that the patient needs in an intensive insulin regimen. When carbohydrates are processed by the digestive system, they are converted into sugar (glucose) and used by the body's cells as energy. Insulin helps to get the glucose into the cells, and the amount of insulin that is needed to do this varies with the amount of carbohydrates that were eaten by the patient. Normally, the pancreas handles the insulin production process. If a patient practices intensive insulin therapy, the patient mimics the effect of the pancreas by counting the amount of carbohydrates he plans to eat and then figuring out how much insulin he will need to manage them (i.e., food dose). The balance of these two amounts is called the patient's carbohydrate-to-insulin ratio. For example, if a patient's personal CIR is one unit of insulin for every 15 grams of carbohydrates, and the total carbohydrate grams in the food he plans to eat is 45 g, he will need three units of insulin to cover the meal. A dietitian or other health care provider generally must explain how to calculate the CIR ratio, which is different for each person, varies with the time of day, may change over time and is difficult to estimate. In addition to knowing planned carbohydrate intake and CIR, a patient needs to factor in how far off their current blood glucose level is from a target level at the beginning of a given meal-time period and take extra insulin if the glucose is high or less insulin if the glucose is low (i.e., correction dose).

Patients will often make corrections to their insulin doses based upon how far their actual premeal blood glucose value is from their premeal target glucose value (i.e., a correction dose). The correction dose is determined by the insulin sensitivity factor, ISF, which is the amount that 1 unit of insulin will lower the blood glucose value, as described in more detail below. The dose is the difference of the current blood glucose value from the target glucose value, divided by the ISF. It may be positive and therefore imply that the patient will take extra insulin, or negative and therefore imply that the patient will reduce their dose of insulin.

Many patients on intensive insulin therapy calculate each insulin dose. The total dose is the food dose plus the correction dose. They count carbohydrates and utilize the carbohydrate-to-insulin ratios (CIRs) when they eat so they can calculate their food dose. In addition, they will make necessary correction to their insulin doses by calculating a correction dose. They take insulin at the proper time before meals (if scheduled) and monitoring their blood sugar level at least four times a day to know what corrections need to be made to their insulin dose. The patient must use a CIR developed for him by his healthcare professionals so that he can use the amount of carbohydrates he plans to eat to determine how much insulin he needs to inject for food. Thus, this method also requires counting carbohydrates. They also must use an ISF developed for him by a healthcare professional so that he can use the variation of current blood glucose from the target value to determine how much insulin he needs to correct for a currently abnormal blood glucose value.

As stated above, home diabetes therapy requires a patient to carry out a prescribed regimen that involves self-testing blood glucose levels and administering appropriate doses of insulin. Glucose levels are monitored at periodic intervals to determine when another insulin injection should be taken or to determine how the user is responding to prior injections. The patient monitors blood levels by lancing a portion of the body with a lancet, for example, to take a blood sample or by using a subcutaneous glucose monitoring device, among other methods. A blood sample drawn, for example, via a lancet is then placed on a test strip that contains appropriate reagents for creating the chemical reactions necessary to measure glucose levels, which is subsequently analyzed by a blood glucose monitor. The patient then manually records the results, the time and date in a log book or in the blood glucose monitor. Alternatively, the blood glucose monitor automatically determines blood glucose levels (e.g., via a subcutaneous sensor) and stores the results and corresponding dates and times in a computerized memory device. The patient then determines the amount of medication (e.g., insulin) needed based on tested blood glucose levels and planned food intake and uses a medication delivery device (e.g., a syringe, medication delivery pen or infusion pump) to deliver the appropriate amount of insulin. The afore-mentioned and commonly assigned U.S. patent application Ser. No. 10/153,883, filed May 24, 2002, discloses a diagnostic and medication delivery system for monitoring blood glucose levels and recording insulin intake, for example. A diagnostic and medication delivery system is also described in commonly assigned U.S. Pat. No. 6,192,891, which is also expressly incorporated herein in its entirety.

Most patients undergoing insulin therapy for managing their diabetes have difficulty determining how much insulin they need. As described above, the dose needed is dependent on how many carbohydrates were ingested over a particular period (e.g., periods extending from breakfast to lunch, lunch to dinner, dinner to snack before bedtime, or periods extending over other mealtimes or snack times), and how far their blood glucose levels are off from a therapeutic target level. In addition to the patients' carbohydrate to insulin ratio (CIR), another important factor for insulin dose determination is insulin sensitivity factor (ISF) or correction factor (CF). The ISF is understood to be the expected drop of glucose concentration when 1 Unit (U) of insulin is administered to a patient. The ISF is individual to the patient and is determined over a period of time. A common ISF is 30-50 mg/dL per unit of insulin. A starting CIR often used is 5-15 grams of carbohydrate per unit of insulin. Both constants (CIR and ISF) may be different for each meal and are adjusted based on current data from blood glucose values, insulin doses and meal sizes. These adjustments are very complex, and few patients understand how to do them. Many healthcare professional also find adjusting these constants to be a daunting process.

Thus, medical nutrition therapy is a critical component of therapy for patients on insulin. While meal portion sizes and estimates of carbohydrate servings (15 grams) and carbohydrate counting are concepts that can be learned, accurate insulin dose determination is too difficult for some patients, even if they are provided with the CIR and ISF. Few patients are capable of accurately determining the CIR and ISF themselves. A patient who finds self-determination of his CIR too difficult may opt to have his CIR determined for him by a healthcare provider. Such a determination of CIR by a healthcare provider also has drawbacks. First, the patient must supply the provider with extensive data relating to blood sugar levels, times of blood glucose testing, results and insulin doses, among other information such as stress level, exercise, and so on, which can be time consuming and inconvenient. Second, a patient may not have any access or sufficiently frequent access to a provider for the provider to be able to make adequate adjustments to the patient's diabetes management formula and/or its various factors (e.g., CIR, ISF and so on). Finally, many providers have difficulty determining these constants from all of the data and tend to guess at the value based upon only one or two data points.

A need therefore exists for a simplified method for patients on insulin therapy and for their healthcare providers to determine their carbohydrate to insulin ratio (CIR) and their insulin sensitivity factor (ISF) from available blood glucose, food and insulin data.

SUMMARY OF THE INVENTION

In accordance with the present invention, an apparatus and method are provided for determining a patient's CIR and ISF, and using these values, along with values for current blood glucose level and deviation from target blood glucose level, for determining insulin dose in view of carbohydrate intake during a particular time period. The present invention is preferably implemented in a diagnostic and/or medication delivery system.

In accordance with an aspect of the present invention, an apparatus and method are provided for (1) storing at least one data set in a memory device, the data set comprising blood glucose readings for, respectively, substantially the beginning of and substantially the end of a selected period of time, a value corresponding to the patient's food intake for the selected period, and the amount of insulin administered to the patient during the selected period; (2) providing an insulin sensitivity factor for the patient based upon the current estimate of the CIR, and the determination of the ISF is based upon the data from the memory device or entered independently into the processing device described below; and (3) determining a carbohydrate to insulin ratio for each data set using the current insulin sensitivity factor and the determination of the CIR is based upon the data from the memory device or entered independently into the processing device described below. The processing device is selected from the group consisting of a personal computer, a personal data assistant, a hand held computing device or other microprocessor-based device, a blood glucose monitor, an infusion pump, a medication delivery pen, a meter, a calculator, a therapeutic device used for managing a patient's blood glucose levels, a diagnostic device used for managing a patient's blood glucose levels, and an informational device used for managing a patient's blood glucose levels. The processing of the data may be iterative or may use sophisticated mathematical techniques known to one skilled in the art.

In accordance with another aspect of the present invention, an apparatus and method are provided for (1) storing at least one data set in a memory device, the data set comprising blood glucose readings for, respectively, substantially the beginning of and substantially the end of a selected period of time, a value corresponding to the patient's food intake for the selected period, and the amount of insulin administered to the patient during the selected period; (2) calculating a delta blood glucose level corresponding to the difference between the blood glucose readings taken, respectively, at substantially the beginning of and substantially the end of the selected period; (3) determining a correct insulin amount using the delta blood glucose level, the current insulin sensitivity factor, and the amount of insulin administered to the patient during the selected period; and (4) determining a plurality of daily carbohydrate to insulin ratios corresponding to respective ones of a plurality of days, the daily carbohydrate to insulin ratios each being based on the correct insulin amount and the value corresponding to the patient's food intake for the selected period from the data set of the corresponding one of the plurality of days. The carbohydrate to insulin ratio for the selected period can be determined from an average of the daily carbohydrate to insulin ratios, including a weighted average of the plurality of daily carbohydrate to insulin ratios. The initial estimate of the insulin sensitivity factor can be generated using at least one number selected from the range of numbers equal to or between 1500 and 1800, and dividing the at least one number by the total daily insulin dose.

In accordance with yet another aspect of the present invention, the apparatus and method are also provided for (5) determining the amount of insulin not needed for carbohydrates consumed on a given day; and (6) determining an estimate of the insulin sensitivity factor for the given day using the delta blood glucose divided by the amount of insulin not needed for the given day. Determining the amount of insulin not needed for carbohydrates consumed on a given day comprises the steps of: (a) determining a carbohydrate to insulin ratio for the selected period from an average of the daily carbohydrate to insulin ratios; (b) dividing the value corresponding to the patient's food intake by the carbohydrate to insulin ratio for the selected period, the value for the patient's food intake being the value for the selected period obtained from the data set of one of the plurality of days corresponding to the given day; and (c) subtracting the result of the dividing step from the actual insulin taken on that given day. The value may be negative (i.e., not enough insulin was taken for the food eaten). The insulin sensitivity factor for the day is the difference of the blood glucose values between the beginning and end of the period divided by the insulin not needed for the ingested carbohydrates.

In accordance with yet another aspect of the present invention, the insulin sensitivity factor for the selected period is determined from an average of the insulin sensitivity factor for each of a plurality of days, and can be a weighted average of the insulin sensitivity factor for each of a plurality of days.

In accordance with other aspects of the present invention, input signals from a user input device may provide user input information selected from the group consisting of the amount of food eaten in the selected period in grams, bread exchanges or units, points or other method of quantitating for food eaten in the selected period, and a carbohydrate to insulin ratio supplied by a health care provider. A conversion operation to convert the user input information to a different unit of measurement can be performed such as conversion operations selected from the group consisting of bread exchanges to grams, grams to bread exchanges, units insulin to milligrams, and milligrams to units insulin.

In accordance with another aspect of the present invention, an apparatus, method and computer readable medium are provided for: (1) storing at least one data set in a memory device, the data set comprising blood glucose readings for, respectively, substantially the beginning of and substantially the end of a selected period of time, a value corresponding to the patient's food intake for the selected period, and the amount of insulin administered to the patient during the selected period; (2) calculating a delta blood glucose level corresponding to the difference between the blood glucose readings taken, respectively, at substantially the beginning of and substantially the end of the selected period; and (3) determining a correct insulin amount using the delta blood glucose level divided by an insulin sensitivity factor, and the result of the division (which may be negative) being added to the amount of insulin administered to the patient during the selected period. The selected period of time corresponds to a period of time occurring within one day, and comprises one meal time selected from the group consisting of breakfast, lunch, dinner, or snack.

Further, the apparatus, method and computer readable medium are provided for: (4) determining a plurality of daily carbohydrate to insulin ratios corresponding to respective ones of a plurality of days, the daily carbohydrate to insulin ratios each being based on the correct insulin amount and the value corresponding to the patient's food intake for the selected period from the data set of the corresponding one of the plurality of days; and (5) determining a carbohydrate to insulin ratio for the selected period from an average of the daily carbohydrate to insulin ratios. Daily carbohydrate to insulin ratios can each be based on the correct insulin amount divided into the value corresponding to the patient's food intake for the selected period from the data set of the corresponding one of the plurality of days.

In accordance with another aspect of the present invention, the apparatus, method and computer readable medium are further provided for: (6) determining the amount of insulin not needed for carbohydrates consumed on a given day; and (7) determining an estimate of the insulin sensitivity factor for the given day using the delta blood glucose divided by the amount of insulin not needed for the given day. Determining the amount of insulin not needed for carbohydrates consumed on a given day can comprise the steps of: (a) dividing the value corresponding to the patient's food intake by the carbohydrate to insulin ratio for the selected period, the value for the patient's food intake being the value for the selected period obtained from the data set of one of the plurality of days corresponding to the given day; and (b) subtracting the result of the dividing step from the an estimate of the insulin sensitivity factor for the given day. The device may also be able to determine values for both carbohydrate to insulin ratios and insulin sensitivity factors that differ temporally according to day of the week, weekdays, weekends, or biological rhythms, such as the menstrual cycle.

BRIEF DESCRIPTION OF THE DRAWINGS

These and other objects, advantages and novel features of the present invention will be readily appreciated from the following detailed description when read in conjunction with the accompanying drawings, in which.

Throughout the drawing figures, like reference numerals will be understood to refer to like parts and components.

DETAILED DESCRIPTION OF THE PREFERRED EMBODIMENTS

As will be described in more detail below, the present invention is generally a method of determining a patient's CIR and ISF, and using these values, along with values for current blood glucose level and deviation from target blood glucose level, for determining insulin dose in view of carbohydrate intake during a particular time period. The present invention is preferably implemented in a diagnostic and/or medication delivery system. The diagnostic system is for monitoring and recording property levels in a patient (e.g., blood glucose levels), as well as medication doses (e.g., insulin) received by the patient. The medication delivery system can be an insulin pump, insulin pen or a device to deliver insulin to the lungs, oral mucosa or for ingestion, or similar devices that are separate from or integrated with the diagnostic system. The diagnostic system can also alert the patient if monitored levels fall outside a clinical target range, and assist a patient with determining corrective action to return the patient to prescribed property levels according to a clinical plan.

Figure 1:
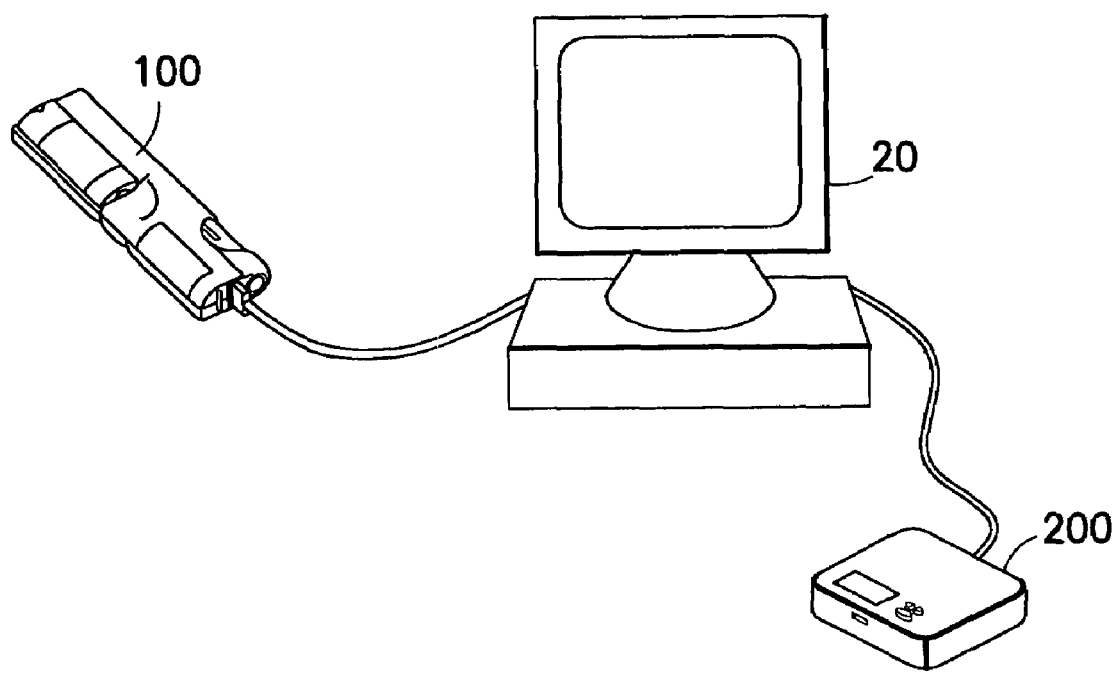
FIG. 1 illustrates exemplary devices in which the algorithms of the present invention can be employed.

More specifically, the present invention is employed in a software program, a programmable device (e.g., personal computer (PC), personal data assistant (PDA) or other hand held computing device, blood glucose monitor (BGM), infusion pump, medication delivery pen, meter, calculator, and so on), or any other therapeutic, diagnostic or informational device that can be used for managing a patient's blood glucose levels. By way of non-limiting examples and with reference to FIG. 1, the present invention can be used with a blood glucose meter 200 or diabetes management system 100 such as, respectively, the BD Logic™ blood glucose monitor or BD Latitude™ diabetes management system, both of which are available from Becton, Dickinson and Company, Franklin Lakes, N.J. Further, the present invention can be used, by way of an example, with a clinical management tool installed on a computer 20 such as the BD™ Diabetes Software that is also available from Becton, Dickinson and Company.

Figure 2:
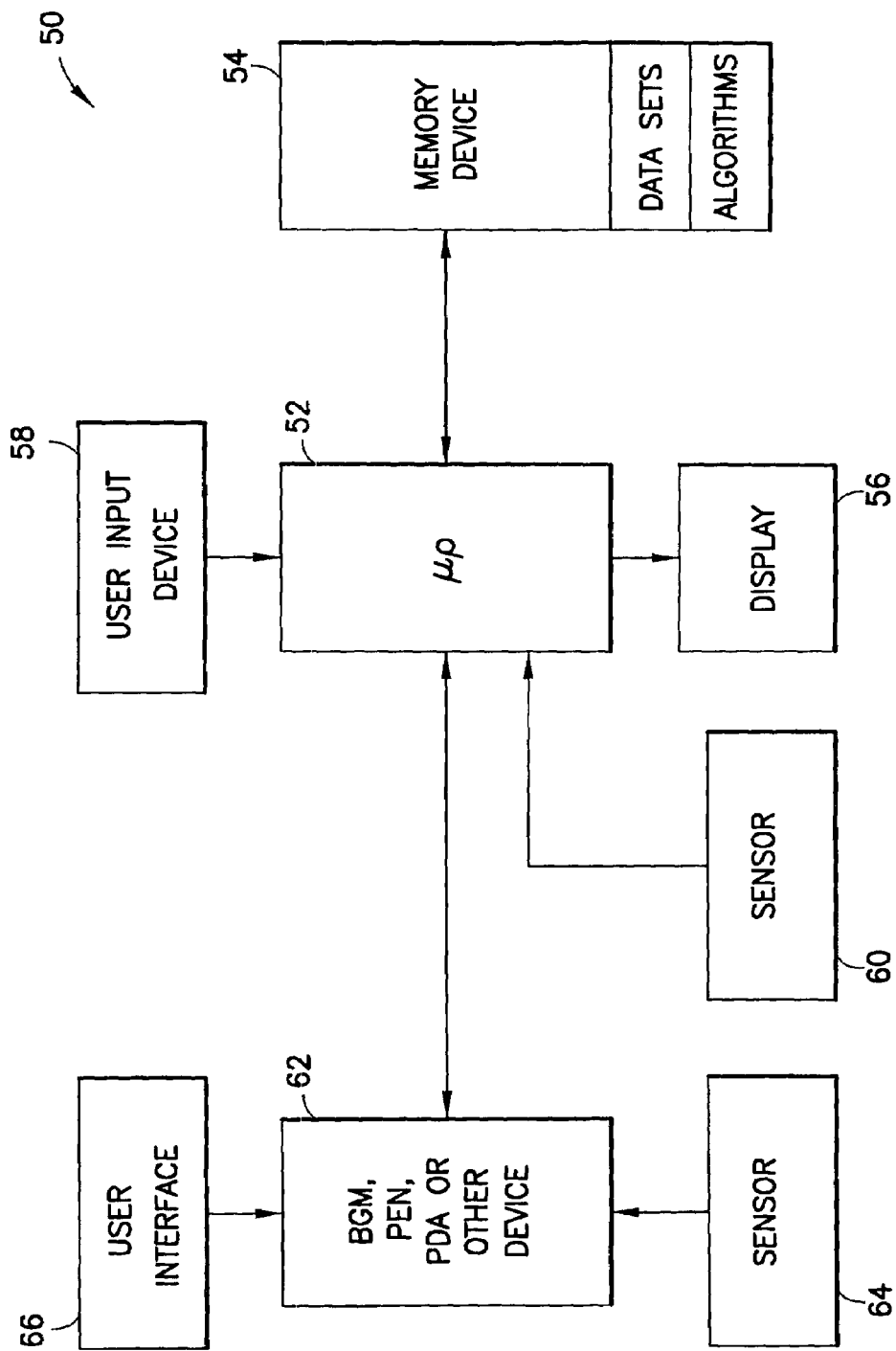
FIG. 2 is a block diagram of an apparatus for determining insulin sensitivity and carbohydrate to insulin ratio in accordance with an embodiment of the present invention.

FIG. 2 is a block diagram of an exemplary apparatus 50 for implementing the present invention. The components of the exemplary apparatus 50 can be provided in different devices such as any of the aforementioned blood glucose meter 200, diabetes management system 100, or computerized clinical management tool 20 shown in FIG. 1. The apparatus 50 preferably comprises a processing device 52 that can be programmed with an algorithm(s) for performing the operations of the present invention, including not but limited to determining CIR, ISF and insulin dosage recommendation based on current or anticipated carbohydrate intake during a selected period, and forwarding information to a user display 56 such as display screens to guide a user when entering information (e.g., blood glucose levels and carbohydrate intake data) and display screens to provide a user with information such as a recommended insulin dosage. The processing device can process the data iteratively or use other mathematical techniques known to one skilled in the art. The processing device 52 can be, for example, a microprocessor, a personal data assistant (PDA), lap top computer or other portable processing device, a personal computer, and a mainframe computer, among other computing devices and may be local to the device or may process the data remotely and transmit the final values back to the initial device. The processing device 52 and the display device 56 can be provided as separate devices in the system 50 or integrated into a single device.

The processing device 52 can be connected to a memory device 54 for storing the algorithms for implementing the present invention and data such as, but not limited to, blood glucose levels, carbohydrate intake data and insulin administration data, optionally the times of insulin administration, and optionally the times the carbohydrates were consumed. The memory unit 54 is formed with memory components, non-limiting examples of which can be a RAM unit, a disk drive unit, a hard disk drive unit, a tape drive unit, or other data storage means, which are well known in the art. It is appreciated that the memory unit 54 may be a discrete component rather than integral with the processing device 52.

With continued reference to FIG. 2, a user can enter information manually via a user input device 58 (e.g., a key pad, keyboard, mouse or other input device), or user information (e.g., blood glucose levels and insulin administration data) can be entered automatically via a sensor 60 (e.g., a blood glucose sensor) or other device 62 comprising a sensor 64 (e.g., an insulin pump with a glucose sensor) and user interface 66. The sensor 60 or 64 can be, for example, a continuous glucose-sensing unit, a semi-continuous glucose-sensing unit, or a discrete glucose-sensing unit. The sensor 60 or 64 can require a body fluid sample for testing. For example, the patient uses a lancet to draw a droplet of blood for blood glucose level testing, or a body fluid sample is collected via an implanted electrochemical device (e.g., intravasal or interstitial). The sensor 60 or 64 can operate electrochemically, via microdialysis, transdermally, or noninvasively. The sensor 60 or 64 can also be a blood glucose monitor, that is, a blood glucose sensor provided along with other processing and input/output components for programmed monitoring.

The processing device 52 can communicate with the memory device 54, the user input device 58, the display 56, the sensor 60 and/or the other device 62 via wired means (e.g., serial ports, parallel ports, and various types of bus architectures) or wireless means (e.g., an ultrasound, infrared, or other radio frequency link). Further, different types of wired or wireless links can be used between the different devices.

The algorithms for implementing the present invention will now be described with reference to the flow chart of FIG. 3. In accordance with a preferred embodiment of the present invention, a plurality of data sets for a given time period (e.g., breakfast to lunch) are used to estimate the CIR and ISF. The memory device 54 stores a sufficient number of data sets to obtain a valid estimate (e.g., at least five data seta and preferably between 10 and 30 data sets). Each data set preferably comprises:

Blood glucose at start of period (n) on day (a) (i.e., value $BG_{an}$, and time $TBG_{an}$);

Blood glucose at end of period (n) on day (a) (value $BG_{an+1}$, and time $TBG_{an+1}$);

Amount of food eaten during period (n) on day (a), in grams, bread exchanges or any other consistent unit (i.e., value $Carb_{an}$ and time $TCarb_{an}$);

Insulin injected or infused, in Units or any other consistent unit (i.e., value $Ins_{an}$ and time $TIns_{an}$); and Time values, which are optional for all data points.

The blood glucose values can be provided by the sensor 60 or other device 62 with sensor 64 automatically or manually (e.g., via a keyboard or other direct, indirect, automatic or manual type of user input device 58). The carbohydrate values are generally provided manually by the user via a keyboard or other type of user input device 58 but could be input automatically, remotely or both. The insulin administration data can be provided automatically (e.g., the device 62 with sensor 64 is an insulin pump or medication delivery pen with automated output feature) or manually (e.g., via a keyboard or other type of user input device 58). The processing device 52 can be provided with different conversion algorithms to accommodate the use of different units for representing carbohydrate intake (e.g., bread exchange units, carbohydrates in grams, and so on) and insulin intake (e.g., insulin Units (U), milligrams, and so on) in the algorithms for implementing the present invention. With continued reference to FIG. 2, the memory device 54 is provided with initial data sets comprising blood glucose levels, insulin intake data and current or anticipated carbohydrate intake data for a selected meal-time period (e.g., a period of time extending from breakfast to lunch, lunch to dinner, dinner to snack before bedtime, or periods extending over other mealtimes or snack times), as indicated in block 70. The integrity of the data for each period is also checked using a set of rules indicating the possible acceptable range of values (i.e., none can be negative). The individual values can also be checked to confirm that they are statistically part of the same population as the previous data.

In addition to the above data sets, an initial estimate of a patient's ISF (block 72 in FIG. 3) is used by the processing device 52, as described in connection with Equation (2) below, in accordance with a preferred embodiment of the present invention. The initial estimate of $ISF_n$ or insulin sensitivity factor, also known as CF or correction factor for a specific time period over multiple days, can come from a number of different sources or methods. For example, the initial $ISF_n$ can be determined from a number (e.g., 1500 or 1800) divided by total daily insulin dose in units, and therefore varies for other estimates of insulin (e.g., insulin measured in mg). The 1500 Rule was developed by Dr. Paul C. Davidson, Medical Director of the Diabetes Treatment Center in Atlanta, Ga., who based it on his experience managing his patients' diabetes. The 1500 Rule is defined as the number of mg/dl the blood glucose level will drop after the administration of one unit of Regular insulin. According to John Walsh, P. A., C. D. E., in his book "Pumping Insulin ($3^{rd}$ edition)", when using a faster-acting insulin (e.g., Humalog), the number 1800 can work better since less faster-acting insulin than Regular insulin is generally needed to lower blood glucose. The user interface (e.g., display 56) provides a screen to guide a patient to enter a number (e.g., 1500, 1800 or other number) via the user input device 58 for estimating the ISF during set-up of the processing device 52 to determine CIR and ISF. $ISF_n$ is then calculated as the average value (which can be weighted) from the data of multiple days at a specific time period(n). $ISF_{an}$ is the estimate from a specific day (a) and time period (n).

Figure 3:
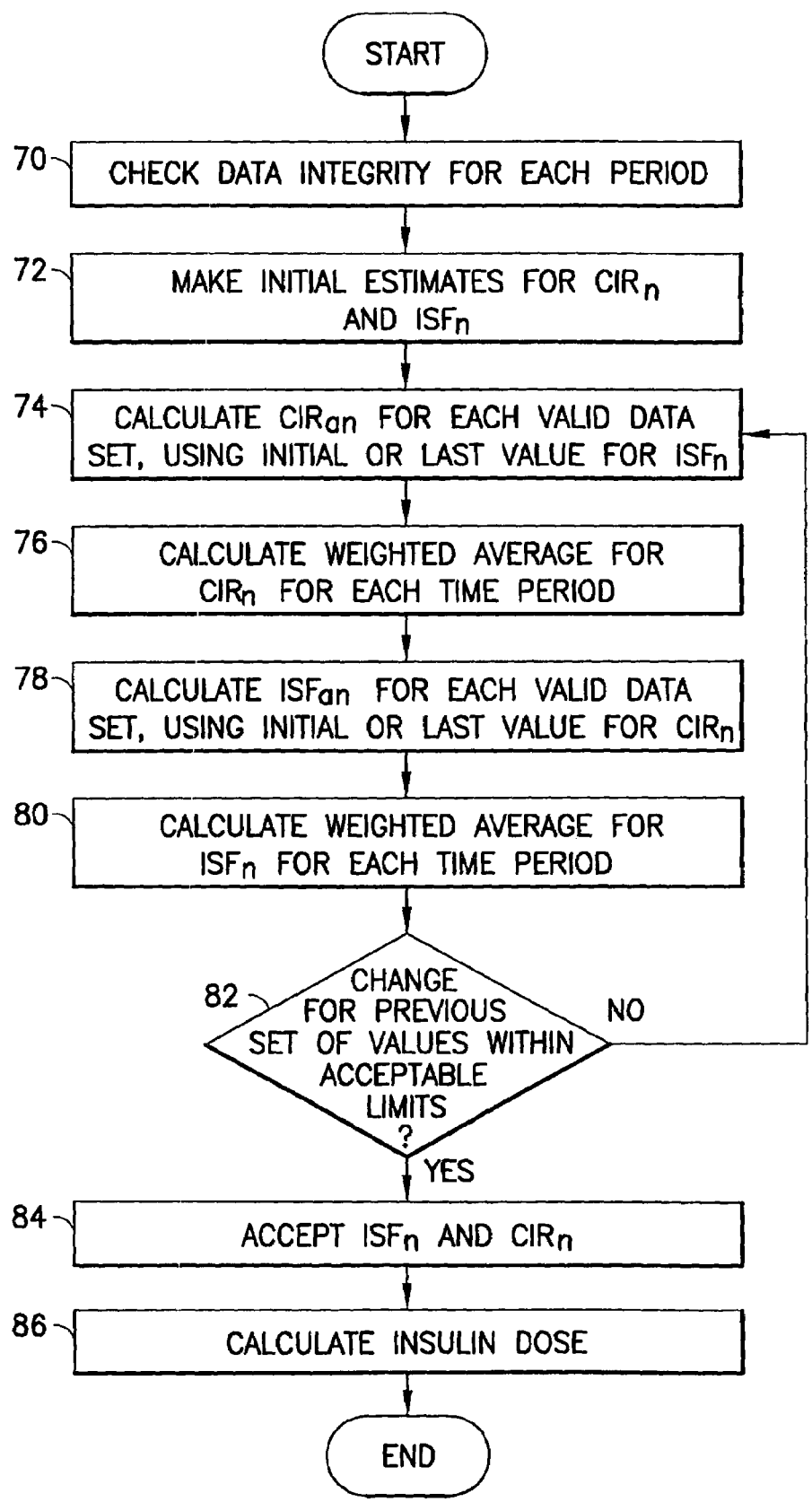
FIG. 3 is a flow chart illustrating a sequence of operations for determining insulin sensitivity and carbohydrate to insulin ratio in accordance with an embodiment of the present invention.

In accordance with the present invention, the $CIR_{an}$ for each valid data set is calculated using an initial or last value for $ISF_n$ (block 74 in FIG. 3). The determination of the CIR is based upon data from the memory device 54 or otherwise entered via the processing device 52 and user input device 58. The weighted average for $CIR_n$ for each time period is then calculated (block 76). The equations employed by the processing device 52 for the estimate of CIR are as follows:

For a given day (a) and period (n), $$\Delta BG_{an} = BGa_{n+1} - BGa_n \qquad \text{(Eqn. 1);}$$

$$CorrIns_{an} = Ins_{an} + \Delta BG_{an}/ISF_n \qquad \text{(Eqn. 2);}$$

$$CIR_{an} = Carb_{an}/CorrIns_{an} \qquad \text{(Eqn. 3); and}$$

$$CIR_n = (\Sigma_a^Z(W_{an} * CIR_{an}))/\Sigma_a^Z(W_{an}) \qquad \text{(Eqn. 4)}$$

$\Delta BG_{an}$ or delta blood glucose is the change in blood glucose during period (n) on day (a). Its constituent values are taken from the afore-mentioned data sets stored in the memory device 54, as are the values for $Ins_{an}$ and $Carb_{an}$. $CorrIns_{an}$ is the amount the patient should have taken so that the blood glucose would not have changed during period (n) on day (a).

$CIR_{an}$ (block 74 in FIG. 3) is the value from the data of a specific day (a) and time period(n). $CIR_n$ (block 76) is the average value (which can be weighted) from the data of multiple days at a specific time period(n). $W_{an}$ is a weighting factor for the day a and period n, and is determined by a series of rules to calculate the relative error in the determination (i.e., if the $CorrIns_{an} = Ins_{an}$, the relative error is low).

In accordance with the present invention, the $ISF_{an}$ for each valid data set is calculated using an initial or last value for $CIR_n$ (block 78 in FIG. 3). The ISF can be based upon the current estimate of the CIR and its determination based upon data from the memory device 54 or otherwise entered via the processing device 52 and user input device 58. The weighted average for $ISF_n$ for each time period is then calculated (block 80). The equations employed by the processing device 52 for the estimate of ISF are as follows:

For a given day (a) and period (n), $$\Delta BG_{an} = BGa_{n+1} - BGa_n \qquad \text{(Eqn. 5);}$$

$$BGIns_{an} = Ins_{an} - Carb_{an}/CIR_n \qquad \text{(Eqn. 6);}$$

$$ISF_{an} = \Delta BG_{an}/BGIns_{an} \qquad \text{(Eqn. 7); and}$$

$$ISF_n = (\Sigma_a^Z(W_{an} * ISF_{an}))/\Sigma_a^Z(W_{an}) \qquad \text{(Eqn. 8).}$$

As stated previously, $\Delta BGan$, the delta blood glucose, is the change in blood glucose during period (n) on day (a). Its constituent values are taken from the afore-mentioned data sets stored in the memory device, as are the values for $Ins_{an}$ and $Carb_{an}$. $BGIns_{an}$ is the amount of insulin that was not needed for the amount of carbohydrate eaten by the patient during period (n) on day (a), and the calculation thereof uses the value of $CIR_n$ (Eqn. 4). As stated above, $ISF_{an}$ (block 78) is the estimate from a specific day (a) and time period (n). The insulin sensitivity factor for the day is the difference between of the blood glucose values between the beginning and the end of the period divided by the insulin not needed for the ingested carbohydrates. $ISF_n$ (block 80) is then calculated as the average value (which can be weighted) from the data of multiple days at a specific time period(n). $W_{an}$ is a weighting factor for the day a and period n.

With continued reference to FIG. 2, the processing device 52 is preferably programmed to determine if the change for the previous set of values (i.e., $CIR_n$ and $ISF_n$) are within acceptable limits (block 82). If not, they are recalculated; otherwise, they are accepted (block 84).

Finally, the processing device 52 can be programmed to use the calculated $CIR_n$ and $ISF_n$ to determine a recommended insulin dose (block 86) based on the carbohydrate intake information provided by the patient for a selected time period (e.g., block 70). Alternatively, the calculated $CIR_n$ and $ISF_n$ can be shown on the display 56 or otherwise annunciated to the patient (e.g., via speech processing and a speaker) to allow the patient to determine the insulin dose for that period. An exemplary equation for determining insulin dose based on calculated $CIR_n$ and $ISF_n$ is as follows:

$$\text{Insulin} = \text{Carb}/\text{CIR} + (\text{Glucose} - \text{Target})/\text{ISF} - (\text{remaining insulin}) \qquad \text{(Eqn. 9)}$$

The programmable device or software program for implementing the present invention can also be configured to determine values for CIRs and ISFs that differ temporally according to the day of the week, weekdays, weekends, biological rhythms (e.g., menstrual cycle), among other factors. In accordance with another aspect of the present invention, an offset value for blood glucose level can be used in conjunction with the equations 1 through 9 described herein in the event that delta blood glucose values are measured over shorter time deltas than the average meal time period (e.g., 4 hours) used for the equations. The above-described method for determining CIR, ISF and insulin dose preferably employs a time delta (e.g., 4 hours) between delta blood glucose values in the data sets that is sufficiently long for the blood glucose level to reach the baseline. In the event, however, that the time delta between delta blood glucose values is shorter, the processing device 52 can be programmed to determine an offset value. For example, if the corrected insulin value CorrIns (Eqn. 2) is 100 after 4 hours, and the delta blood glucose value is taken over a 2 hour interval, the processing device 52 can be programmed to determine and use an offset value of 50.

Figure 4:
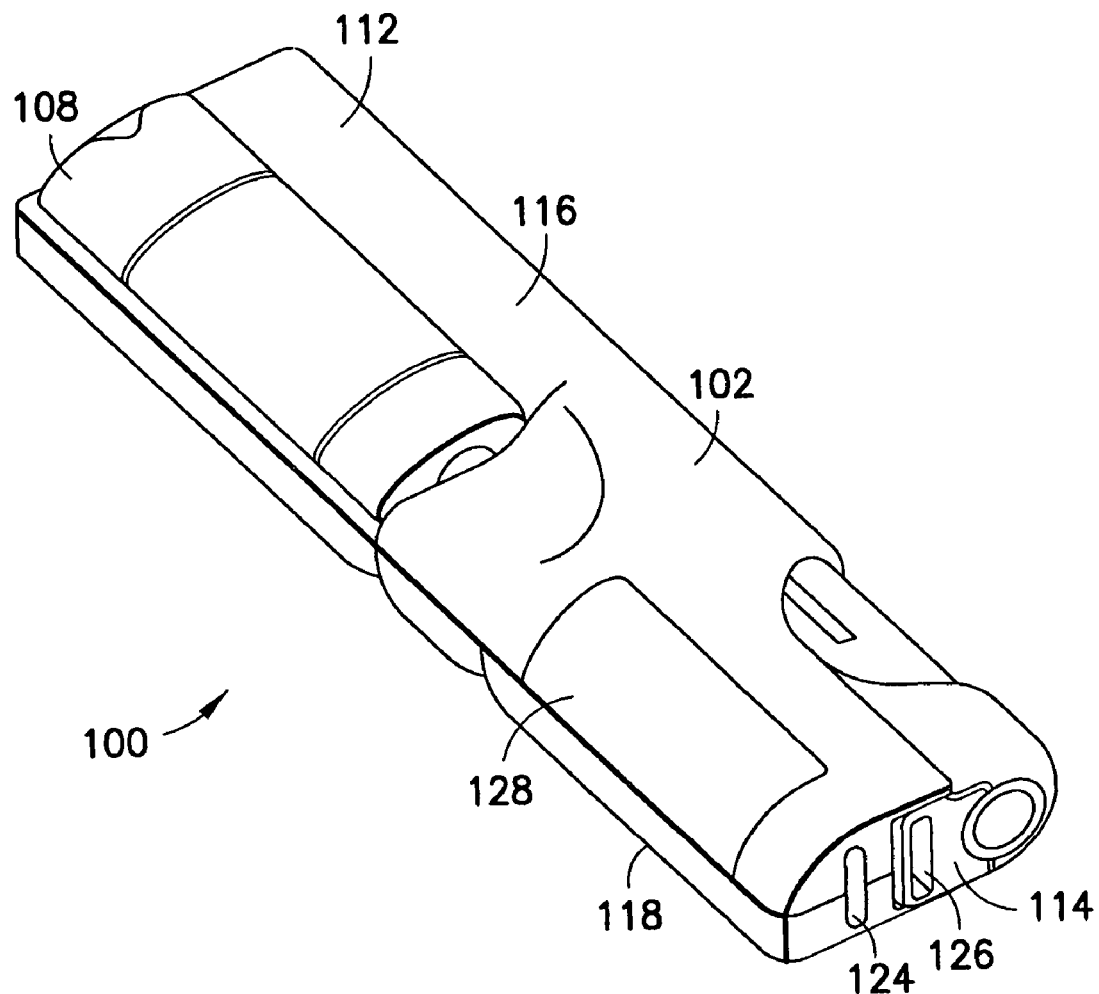
FIGS. 4 and 5 illustrate a device for medication delivery, measurement of a property, storage of dosage and property data and determination of insulin sensitivity and carbohydrate to insulin ratio in accordance with an embodiment of the present invention.
Figure 5:
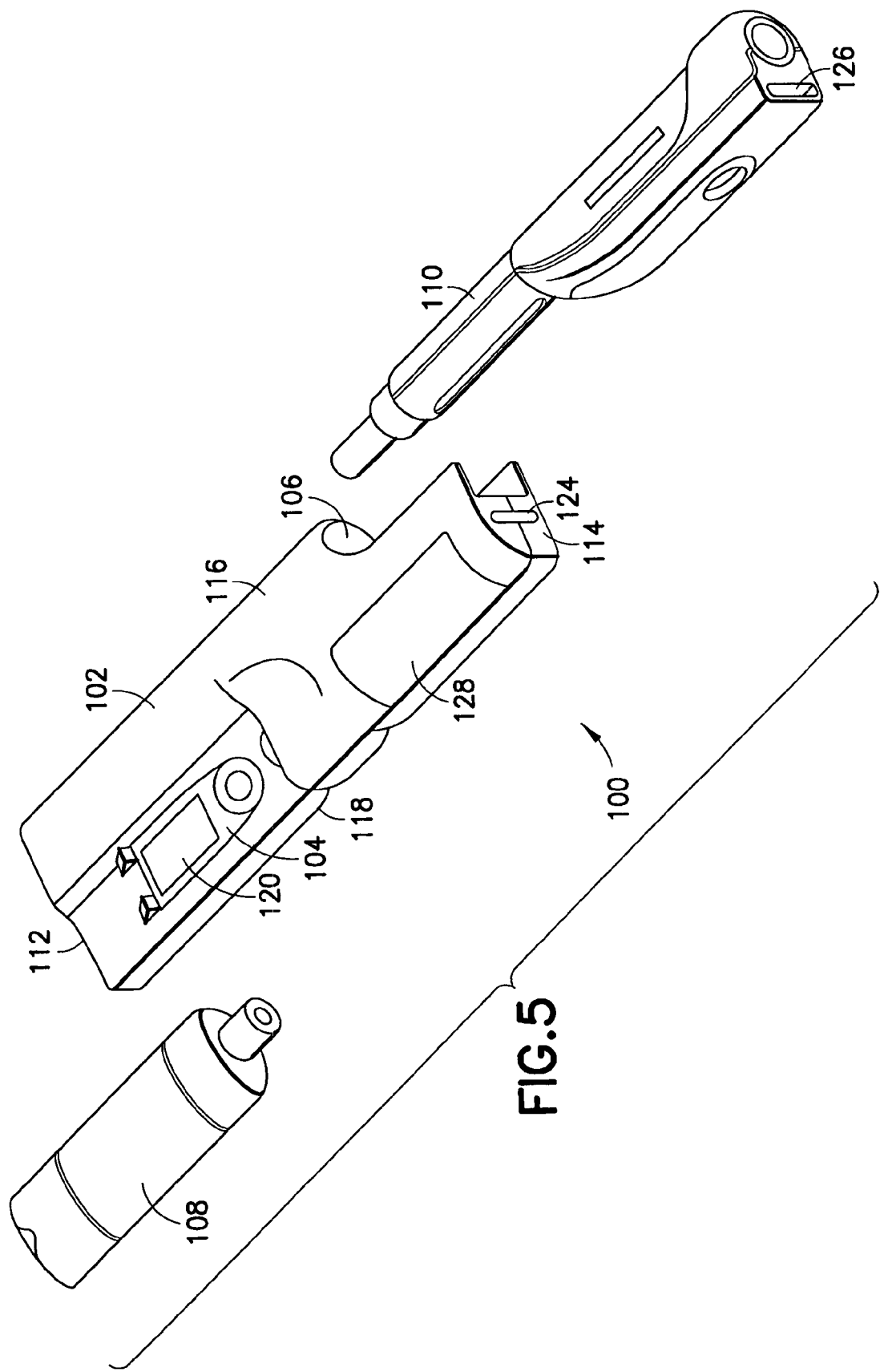

FIGS. 4 and 5 illustrate an exemplary device in which the present invention can be implemented for assisting a patient with diabetes management. The system 100 illustrated in FIGS. 4 and 5 conveniently integrates a medication delivery pen, blood glucose monitor, and lancet into a single portable unit. The system 100 includes a housing 102 that provides mounting locations for a medication delivery pen, lancet, and glucose monitoring meter. Specifically, a lancet compartment 104 and pen compartment 106 are integrally formed with and embedded in the housing 102. The lancet compartment 104 is configured to receive a lancet 108 so that the lancet engages and slides in the lancet compartment in a manner that allows it to be easily inserted and removed. Likewise, the pen compartment 106 is configured to receive a medication delivery pen 110. When inserted in their respective compartments, a portion of the body of the lancet and pen are exposed so that they are readily accessible to the user. However, the compartments each include portions that extend internal to the housing 102 in which the lancet of the lancet and the needle of the pen are to be situated. Accordingly, the lancet and needle are protected by the housing 102 from environmental contamination. Thus, housing 102 provides protection to the needle of the pen, eliminating the need for a separate pen cap. Typically when not in use, a conventional lancet is stored with an open port or cover that exposes the lancet to the environment for possible contamination. However, when packaged in housing 102 of the present invention, the lancing port is completely covered providing protection from the environment to the lancet.

The medication delivery pen 110 may be of any type known to those of ordinary skill in the art. In general, the pen has a drive mechanism for accurate dosing and ease of use. A dosage mechanism such as a rotatable knob allows the user to accurately adjust the amount of medication that will be injected by the pen from a prepackaged vial of medication. To inject the dose of medication, the user inserts the needle under the skin and depresses the knob once as far as it will depress. The pen may be an entirely mechanical device or it may be combined with electronic circuitry to accurately set and/or indicate the dosage of medication that is injected into the user. The electronic circuitry may also serve to record data such as the date, time, amount of medication injected, and so on. The data can be displayed on a display located on the pen. The display may be a mechanical display or an electronic display, depending on whether the pen is a mechanical or electronic pen. The information can also be downloaded via a data port 126 to a computer or other electronic storage device so that it may be subsequently reviewed by the user or a health professional. Data port 126 is preferably an electronic connector, but as will be appreciated by those of skill in the art, an infrared port or any wireless port could be substituted to perform a data exchange function without departing from the present invention. Likewise, data may be uploaded to the pen via data port 126 to install, for example, updated software. Examples of medication delivery pens that may be employed in the present invention are disclosed in U.S. Pat. Nos. 5,536, 249, 5,827,232 and 5,582,598.

Similar to the medication delivery pen 110, the lancet 108 may be of any type known to those of ordinary skill in the art. The lancet 108 will typically include an actuator such as a button for actuating a mechanism that displaces a disposable lancet. The mechanism also returns the lancet to its initial position after it has been inserted into the finger of the user.

A glucose monitor is integrated into housing 102. The glucose monitor includes a display 120, a reaction chamber (not shown) disposed in the housing 102, and a test strip interface 122. The test strip interface 122 is located on the first end 112 of the housing 102 proximate the lancet compartment 104. A disposable test strip on which a blood sample is placed is inserted into the test strip interface 122. When a blood sample enters into the reaction chamber, the blood glucose level is measured using well-known electrochemical or reflectance techniques. In some embodiments of the invention, electrochemical techniques are preferred because they require a relatively small sample of blood, employ a small test strip, and provide a quick response.

Electronics such as a microprocessor and other components, e.g., batteries, associated with the glucose monitor are located in the enclosure of housing 102. The electronic circuitry determines and stores the blood glucose level analyzed in the reaction chamber. A bidirectional data port 124 located on the housing 102 is coupled to the electronic circuitry for transferring data to or from an external device such as a computer, phone jack or a communication network. It should be noted that in some embodiments of the invention employing an electronic medication delivery pen having downloading capabilities, data ports 124 and 126 may be combined so that only a single port is required on housing 102. Moreover, aside from the data ports, the electronic pen and glucose monitor also may be in communication with one another both to share data and eliminate redundant components. For example, a single display may be provided on the housing for displaying the data from both the glucose monitor and the electronic pen. Furthermore, some embodiments of the invention may employ a third display that integrates and displays the data from both the electronic pen and the glucose monitor.

In those embodiments of the invention that employ a mechanical delivery pen, the display located on the housing may be configured so that it automatically switches between two modes. In the first mode, when the pen is installed in the compartment 106 the display displays the blood glucose data. When the pen is removed from its compartment, the display switches to a mode that allows information from the medication delivery pen to be manually entered. This allows the patient to use the invention as a simple electronic log book to recall data from memory. Specifically, the user can enter the number of insulin units that are injected so that this data is stored in the electronics associated with the glucose monitor for subsequent downloading. This arrangement eliminates the need for manually recording the insulin dosage, which would otherwise be required with a mechanical pen. After the pen has been reinstalled in its compartment, the display automatically returns to displaying glucose levels. In addition, the display 106 and buttons can be configured to allow entry of carbohydrates (CARB) and calculation of the dose of insulin from Equation (9) or a similar equation.

In the particular embodiment of the invention shown in FIGS. 4 and 5 the display 120 of the glucose monitor is located in the lancet compartment 104 and forms a portion of the inner surface defining lancet compartment 104. Accordingly, the display 120 is only accessible when the lancet 108 has been removed from the lancet compartment 104 and is therefore protected when the lancet 108 is in place.

The housing 102 may optionally include an accessory compartment 128 for storing such ancillary items as test strips, lancets, and needles. The test strips may be housed in a container that itself is stored in the accessory compartment 128.

Figure 6A:
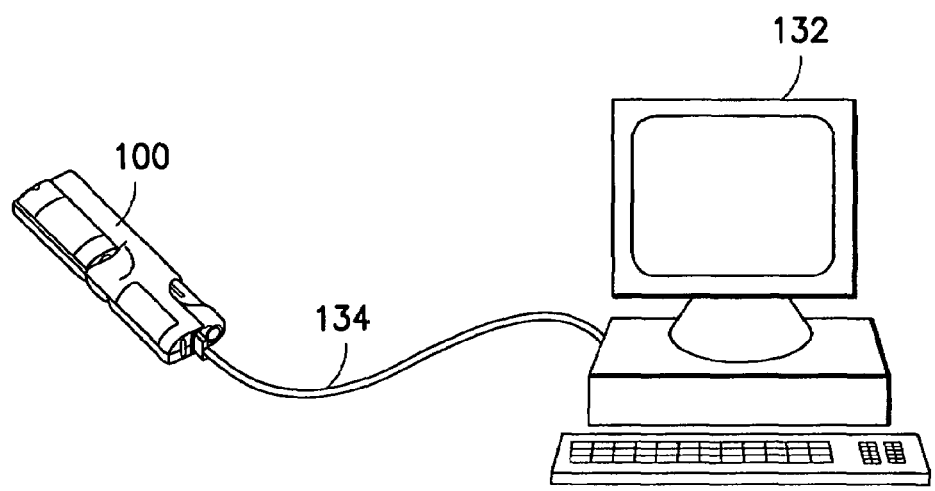
FIGS. 6A, 6B and 6C illustrate various embodiments of the device of FIGS. 4 and 5 connected to a computer for data transfer and enhanced analysis.
Figure 6B:
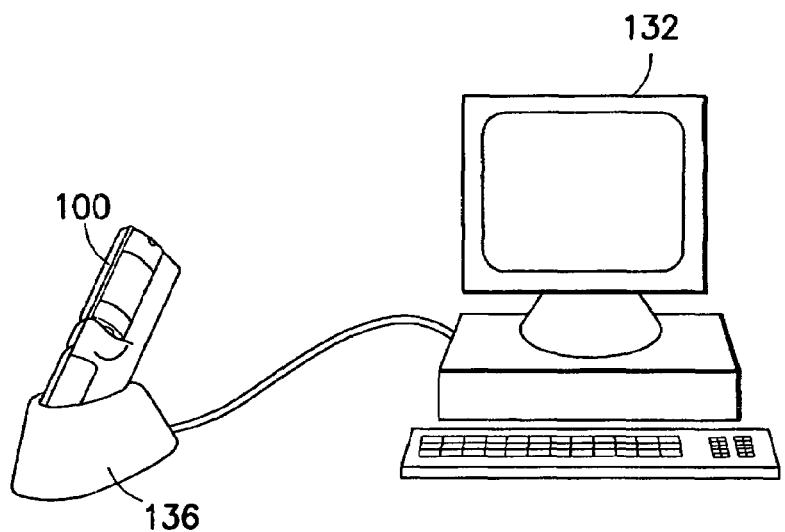
Figure 6C:
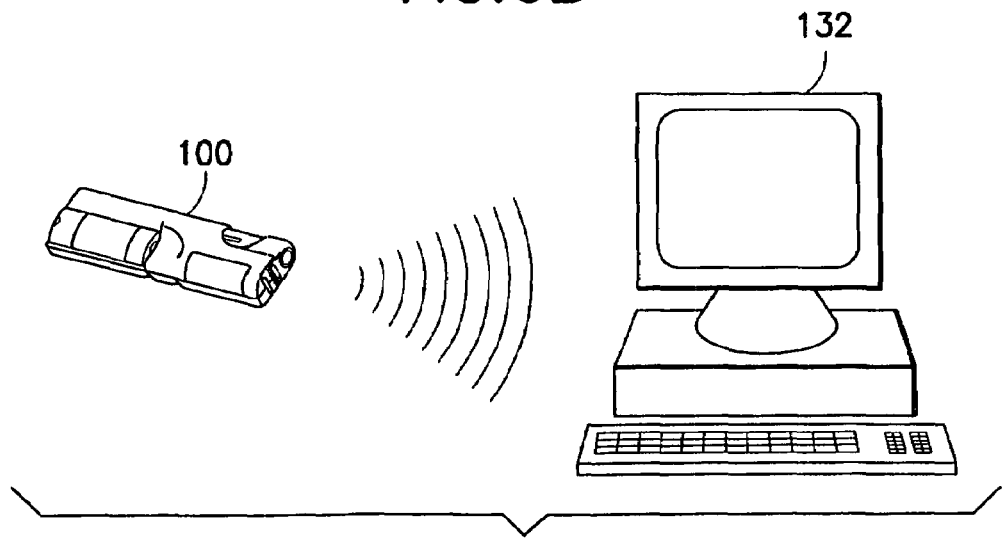

The above described diagnostic and medication delivery system 100 is enhanced to monitor dosage and patient data and notify the patient if they stray from their therapy target. As shown in FIGS. 6A-6C, the device is connected to a computer 132 through data port 124 as described above. In this manner, specific therapy regimen can be programmed into the system at startup, and data from the device can be transferred to a PC 132 over a network for detailed analysis.

FIG. 6A illustrates the device 100 connected to a computer 132 through a cable 134 with a connector adapted to connect to data port 124. FIG. 6B illustrates the device 100 connected to computer 132 through a convenient cradle 136 adapted to accept and support the device 100 while at the same time making an appropriate electrical connection to data port 124. FIG. 6C illustrates a wireless connection between device 100 and computer 132. The wireless connection can be implemented through an infrared transmitter/receiver, or through any other wireless communication method such as, for example, through the Bluetooth or 802.11b protocols. The algorithms described above in connection with FIG. 3 for implementing the present invention can be provided in the electronics of the device 100 or in the computer 132, for example. Thus, the keyboard of the computer 132 can be used to enter the initial data sets and estimated ISF, among other data.

The diagnostic and medication delivery system 100 is particularly advantageous when used in conjunction with a disease management paradigm. Preferably in connection with a consultation with a health care provider, the device 100 is programmed with specific therapy regimen data. The device 100 can assess progress verses targets with each self-monitored blood glucose (SMBG) reading, and deviation from targets causes intervention in real time. Further more, the definition of "deviating from target" can be as sophisticated as necessary. The device 100 can alert the user, not only if the target is missed on a particular reading, but also if the historical data stored in the unit indicates failure to progress towards the target, consistent-prandial highs, or the interaction of dose levels and glucose measures, for example.

If an alert is necessary, the patient simply connects the data port 124 to a PC 132 or communication network, as appropriate, to receive more sophisticated analysis, and opportunity for self-assessment of performance related to key factors, and suggestions for actions to take to improve performance. The connection can be made through an appropriately configured cradle for the device, a cable, or an IR or other wireless link.

Figure 7:
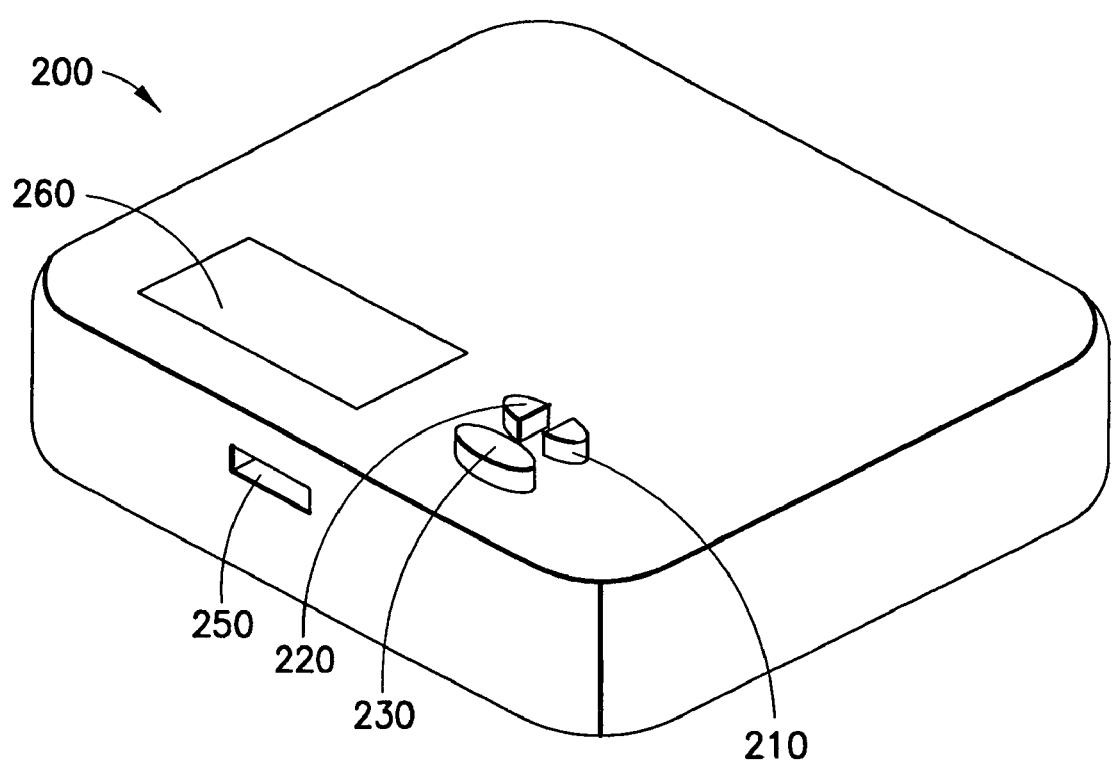
FIG. 7 is a perspective view of an exemplary blood glucose meter in which the algorithms of the present invention can be employed.

With reference to FIG. 7, the apparatus 50 can be implemented at least in part in an exemplary blood glucose meter 200 that has a blood glucose sensing area 250 for the monitoring of glucose within a patient. Blood glucose sensing area 250 may utilize a variety of well known means for the monitoring of glucose within a patient. One method may be the use of a disposable strip with reagents applied thereto for the sensing of glucose within a bodily fluid. In an alternate embodiment of the present invention, sensing area 250 could utilize well known non-invasive sensing methods for the determination of glucose within a patient's body. Sensing of glucose by sensing area 250 can be intermittent or continuous. Blood glucose meter 200 also can be configured to be wearable by the patient and may communicate with other devices such as an insulin pump by infrared, RF or other communications protocol.

Figure 8:
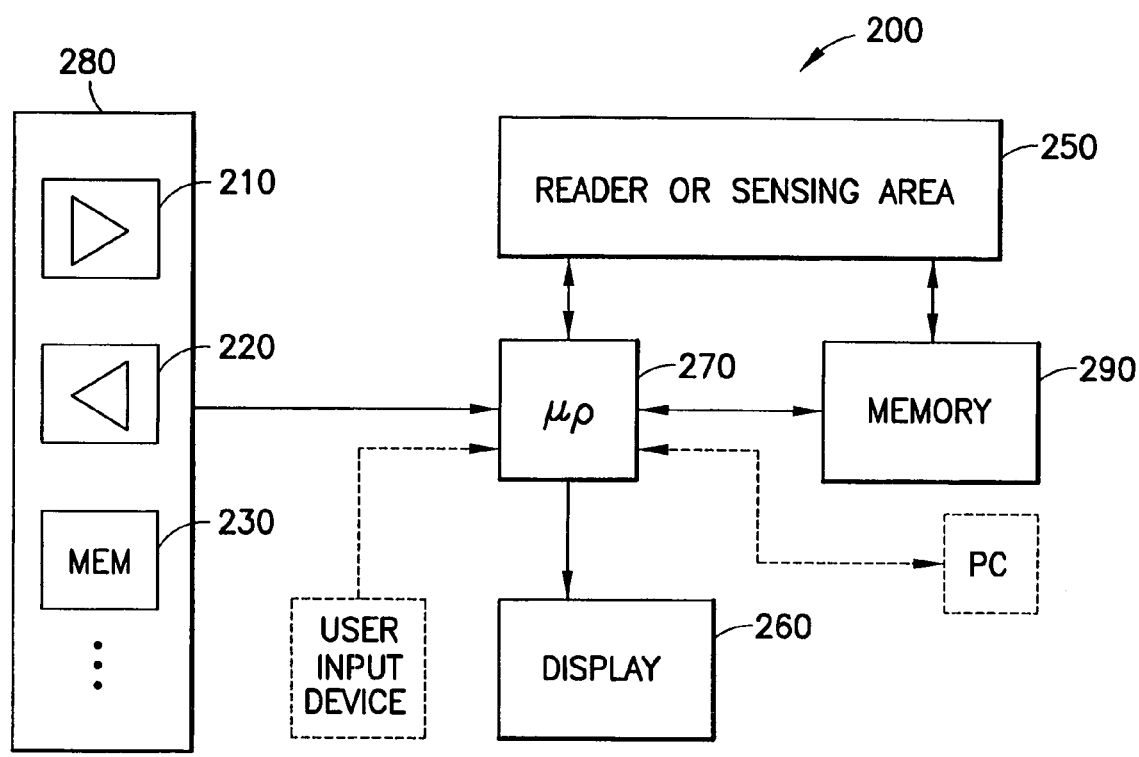
FIG. 8 is a block diagram of the blood glucose meter of FIG. 7.

With reference to FIGS. 7 and 8, blood glucose meter 200 also has a liquid crystal display (LCD) or other type of display device 260 which communicates data within the blood glucose meter 200 to the patient through a variety of menus programmed within the software/program instructions contained within the microprocessor 270 (FIG. 8) of blood glucose meter 200 or stored in the memory device 290 for execution by the microprocessor 270. Alternatively, the meter 200 can annunciate blood glucose values and other information audibly via a speech processing device and speaker. The memory device 290 can store the blood glucose values measured by the reader or other sensing device 250, along with the dates and times of day they were measured, the CIR from a healthcare provider, and calculated values such as the $CIR_n$ and $ISF_n$ determined in accordance with the present invention, among other information. It is to be understood that other memory configurations can be used without departing from the scope of the present invention.

Blood glucose meter 200 also has a variety of input buttons 210, 220, 230 which allow the patient to move through various screens displayed on LCD 260 to view various data within blood glucose meter 200. Forward button 210 and backward button 220 allow patients to move forward and backward through the menu screens shown on LCD 260. Also shown on blood glucose meter 200 is a memory button 230 which allows the user to enter the various menus generated by the software/program instructions of blood glucose meter 200. At least one input button is required; however, alternate embodiments which contain one or more input buttons with different functions are still within the scope of the present invention. Accordingly, a user input device is indicated generally at 280 in FIG. 2. Input may also be through communication with another device or by spoken commands.

The microprocessor 270 can be provided with the algorithms described above in connection with FIG. 3. The data sets can be provided to the memory device 290 via a series of operations using the input buttons 210, 220, 230, from another processing device (e.g., a personal computer or PDA) via a port on the meter 200 by data transmission or via a keyboard via a port on the meter 200.

Although the present invention has been described with reference to preferred embodiments thereof, it will be understood that the invention is not limited to the details thereof. Various modifications and substitutions will occur to those of ordinary skill in the art. All such substitutions are intended to be embraced within the scope of the invention as defined in the appended claims.

What is claimed is:

1. An apparatus for determining factors for insulin therapy comprising:
   a memory device storing at least one data set, the data set comprising blood glucose readings for, respectively, substantially the beginning of and substantially the end of a selected period of time, a value corresponding to the patient's food intake for the selected period, and the amount of insulin administered to the patient during the selected period; and
   a processing device programmed to use an insulin sensitivity factor for the patient wherein the initial insulin sensitivity factor can be one of an estimated insulin sensitivity factor, the most recently known insulin sensitivity factor, and an initial insulin sensitivity factor, and to determine a carbohydrate to insulin ratio for the at least one data set using the insulin sensitivity factor;
   wherein said processing device is programmed to determine a weighted average for a carbohydrate to insulin ratio for a selected time period using the carbohydrate to insulin ratio for each of respective data sets.

2. An apparatus for determining factors for insulin therapy comprising:
   a memory device storing at least one data set, the data set comprising blood glucose readings for, respectively, substantially the beginning of and substantially the end of a selected period of time, a value corresponding to the patient's food intake for the selected period, and the amount of insulin administered to the patient during the selected period; and a processing device programmed to use an insulin sensitivity factor for the patient wherein the initial insulin sensitivity factor can be one of an estimated insulin sensitivity factor, the most recently known insulin sensitivity factor, and an initial insulin sensitivity factor, and to determine a carbohydrate to insulin ratio for the at least one data set using the insulin sensitivity factor;

wherein said processing device is programmed to determine an insulin sensitivity factor for each data set using a carbohydrate to insulin ratio for the patient wherein the carbohydrate to insulin ratio can be an estimated carbohydrate to insulin ratio, the most recently known carbohydrate to insulin ratio, an initial carbohydrate to insulin ratio, the carbohydrate to insulin ratio determined for a data set, and a weighted average for a carbohydrate to insulin ratio for a selected time period using the carbohydrate to insulin ratio for each of respective data sets.

3. An apparatus as claimed in claim 2, wherein said processing device is programmed to determine a weighted average for an insulin sensitivity factor for a selected time period using the insulin sensitivity factor for each of respective data sets.

4. An apparatus as claimed in claim 1,
wherein said processing device is selected from the group consisting of a personal computer, a personal data assistant, a hand held computing device, a blood glucose monitor, an infusion pump, a medication delivery pen, a meter, a calculator, a therapeutic device used for managing a patient's blood glucose levels, a diagnostic device used for managing a patient's blood glucose levels, and an informational device used for managing a patient's blood glucose levels.

5. An apparatus for determining factors for insulin therapy comprising:
a memory device storing at least one data set in a memory device, the data set comprising blood glucose readings for, respectively, substantially the beginning of and substantially the end of a selected period of time, a value corresponding to the patient's food intake for the selected period, and the amount of insulin administered to the patient during the selected period; and
a processing device connected to the memory device and programmed to calculate a delta blood glucose level corresponding to the difference between the blood glucose readings taken, respectively, at substantially the beginning of and substantially the end of the selected period, to determine a correct insulin amount using the delta blood glucose level, an insulin sensitivity factor, and the amount of insulin administered to the patient during the selected period, and to determine a plurality of daily carbohydrate to insulin ratios corresponding to respective ones of a plurality of days, the daily carbohydrate to insulin ratios each being based on the correct insulin amount and the value corresponding to the patient's food intake for the selected period from the data set of the corresponding one of the plurality of days.

6. An apparatus as claimed in claim 5, wherein the processing device is programmed to determine a carbohydrate to insulin ratio for the selected period from an average of the daily carbohydrate to insulin ratios.

7. An apparatus as claimed in claim 5, wherein the processing device is programmed to determine a carbohydrate to insulin ratio for the selected period by calculating a weighted average of the plurality of daily carbohydrate to insulin ratios.

8. An apparatus as claimed in claim 5, wherein the processing device is programmed to generate an initial estimate of the insulin sensitivity factor using at least one number selected from the range of numbers equal to or between 1500 and 1800, and dividing the at least one number by the daily insulin dose.

9. An apparatus as claimed in claim 5, wherein the processing device is further programmed to determine the amount of insulin not needed for carbohydrates consumed on a given day, and an estimate of the insulin sensitivity factor for the given day using the delta blood glucose divided by the amount of insulin not needed for the given day.

10. An apparatus as claimed in claim 5, wherein the processing device is programmed to determine the amount of insulin not needed for carbohydrates consumed on a given day by determining a carbohydrate to insulin ratio for the selected period from an average of the daily carbohydrate to insulin ratios, dividing the value corresponding to the patient's food intake by the carbohydrate to insulin ratio for the selected period, the value for the patient's food intake being the value for the selected period obtained from the data set of one of the plurality of days corresponding to the given day, and subtracting the result of the dividing step from the an estimate of the insulin sensitivity factor for the given day.

11. An apparatus as claimed in claim 5, wherein the processing device is programmed to determine the insulin sensitivity factor for the selected period from an average of the insulin sensitivity factor for each of a plurality of days.

12. An apparatus as claimed in claim 5, wherein the processing device is programmed to determine an insulin sensitivity factor for the selected period by calculating a weighted average of the insulin sensitivity factor for each of a plurality of days.

13. A computer readable medium of instructions to determine factors used for insulin therapy comprising:
a first set of instructions to store at least one data set in a memory device, the data set comprising blood glucose readings for, respectively, substantially the beginning of and substantially the end of a selected period of time, a value corresponding to the patient's food intake for the selected period, and the amount of insulin administered to the patient during the selected period;
a second set of instructions to calculate a delta blood glucose level corresponding to the difference between the blood glucose readings taken, respectively, at substantially the beginning of and substantially the end of the selected period; and
a third set of instructions to determine a correct insulin amount using the delta blood glucose level divided by an insulin sensitivity factor, and the result of the division being added to the amount of insulin administered to the patient during the selected period.

14. A computer readable medium as claimed in claim 13, wherein the selected period of time corresponds to a period of time occurring within one day.

15. A computer readable medium as claimed in claim 13, wherein the selected period of time comprises one meal time selected from the group consisting of breakfast, lunch, dinner, or snack.

16. A computer readable medium as claimed in claim 13, further comprising a fourth set of instructions to generate an initial estimate of the insulin sensitivity factor using at least one number selected from the range of numbers equal to or between 1500 and 1800, and dividing the at least one number by the daily insulin dose.

17. A computer readable medium as claimed in claim 13, further comprising:
a fourth set of instructions to determine a plurality of daily carbohydrate to insulin ratios corresponding to respective ones of a plurality of days, the daily carbohydrate to insulin ratios each being based on the correct insulin amount and the value corresponding to the patient's food intake for the selected period from the data set of the corresponding one of the plurality of days; and a fifth set of instructions to determine a carbohydrate to insulin ratio for the selected period from an average of the daily carbohydrate to insulin ratios.

18. A computer readable medium as claimed in claim 17, wherein said fifth set of instructions comprises instructions to calculate a weighted average of the plurality of daily carbohydrate to insulin ratios.

19. A computer readable medium as claimed in claim 13, further comprising a fourth set of instructions to determine a plurality of daily carbohydrate to insulin ratios corresponding to respective ones of a plurality of days, the daily carbohydrate to insulin ratios each being based on the correct insulin amount divided into the value corresponding to the patient's food intake for the selected period from the data set of the corresponding one of the plurality of days.

20. A computer readable medium as claimed in claim 19, further comprising a fifth set of instructions to determine a carbohydrate to insulin ratio for the selected period from an average of the daily carbohydrate to insulin ratios.

21. A computer readable medium as claimed in claim 20, further comprising:
    a sixth set of instructions to determine the amount of insulin not needed for carbohydrates consumed on a given day; and
    a seventh set of instructions to determine an estimate of the insulin sensitivity factor for the given day using the delta blood glucose divided by the amount of insulin not needed for the given day.

22. A computer readable medium as claimed in claim 21, further comprising an eighth set of instructions to determine the insulin sensitivity factor for the selected period from an average of the insulin sensitivity factor for each of a plurality of days.

23. A computer readable medium as claimed in claim 22, wherein the eighth set of instructions comprises instructions to determine an insulin sensitivity factor for the selected period by calculating a weighted average of the insulin sensitivity factor for each of a plurality of days.

24. An apparatus for determining factors used for insulin therapy comprising:
    a memory device storing at least one data set in a memory device, the data set comprising blood glucose readings for, respectively, substantially the beginning of and substantially the end of a selected period of time, a value corresponding to the patient's food intake for the selected period, and the amount of insulin administered to the patient during the selected period; and
    a processing device connected to the memory device and programmed to calculate a delta blood glucose level corresponding to the difference between the blood glucose readings taken, respectively, at substantially the beginning of and substantially the end of the selected period, and to determine a correct insulin amount using the delta blood glucose level divided by an insulin sensitivity factor, and the result of the division being added to the amount of insulin administered to the patient during the selected period.

25. An apparatus as claimed in claim 24, wherein the selected period of time corresponds to a period of time occurring within one day.

26. An apparatus as claimed in claim 24, wherein the selected period of time comprises one meal time selected from the group consisting of breakfast, lunch, dinner, or snack.

27. An apparatus as claimed in claim 24, wherein the processing device is further programmed to generate an initial estimate of the insulin sensitivity factor using at least one number selected from the range of numbers equal to or between 1500 and 1800, and divide the at least one number by the daily insulin dose.

28. An apparatus as claimed in claim 24, wherein the processing device is programmed to
    determine a plurality of daily carbohydrate to insulin ratios corresponding to respective ones of a plurality of days, the daily carbohydrate to insulin ratios each being based on the correct insulin amount and the value corresponding to the patient's food intake for the selected period from the data set of the corresponding one of the plurality of days, and
    determine a carbohydrate to insulin ratio for the selected period from an average of the daily carbohydrate to insulin ratios.

29. An apparatus as claimed in claim 28, wherein the processing device is programmed to determine a carbohydrate to insulin ratio for the selected period by calculating a weighted average of the plurality of daily carbohydrate to insulin ratios.

30. An apparatus as claimed in claim 24, wherein the processing device is programmed to determine a plurality of daily carbohydrate to insulin ratios corresponding to respective ones of a plurality of days, the daily carbohydrate to insulin ratios each being based on the correct insulin amount divided into the value corresponding to the patient's food intake for the selected period from the data set of the corresponding one of the plurality of days.

31. An apparatus as claimed in claim 30, wherein the processing device is programmed to determine a carbohydrate to insulin ratio for the selected period from an average of the daily carbohydrate to insulin ratios.

32. An apparatus as claimed in claim 31, wherein the processing device is programmed to:
    determine the amount of insulin not needed for carbohydrates consumed on a given day; and
    determine an estimate of the insulin sensitivity factor for the given day using the delta blood glucose divided by the amount of insulin not needed for the given day.

33. An apparatus as claimed in claim 32, wherein the processing device is programmed to determine the insulin sensitivity factor for the selected period from an average of the insulin sensitivity factor for each of a plurality of days.

34. An apparatus as claimed in claim 33, wherein the processing device is programmed to determine wherein the step of determining an insulin sensitivity factor for the selected period by calculating a weighted average of the insulin sensitivity factor for each of a plurality of days.

* * * * *